United States Patent [19]

Bayssat et al.

[11] Patent Number: 4,554,273
[45] Date of Patent: Nov. 19, 1985

[54] 2-AMINO-5-PHENYL-1,3-BENZODIAZEPINES

[75] Inventors: Michel Bayssat, Charbonnieres; Gerard Ferrand; Jean-Claude Depin, both of Lyons, all of France

[73] Assignee: Lipha Lyonnaise Industrielle Pharmaceutique, Paris, France

[21] Appl. No.: 578,046

[22] Filed: Feb. 7, 1984

[30] Foreign Application Priority Data

Feb. 16, 1983 [FR] France .................. 83 02475

[51] Int. Cl.[4] .................. A61K 31/55; C07D 243/04; C07D 403/12; C07D 403/04
[52] U.S. Cl. .................. 514/221; 260/239 BD; 260/330.9; 544/359; 548/518
[58] Field of Search .................. 260/239 BD, 330.9; 424/244; 544/359; 546/271; 548/518

[56] References Cited

U.S. PATENT DOCUMENTS

| 3,681,340 | 8/1972 | Rodriguez et al. | 260/239 BD |
| 3,780,023 | 12/1973 | Suh et al. | 260/239 BD |
| 3,780,024 | 12/1973 | Suh et al. | 260/239 BD |
| 3,838,122 | 9/1974 | Suh et al. | 260/239 BD |

OTHER PUBLICATIONS

Diazepam, The Merck Index, 9th Edition, 1976, p. 394, No. 2961.

*Primary Examiner*—Robert T. Bond
*Attorney, Agent, or Firm*—Browdy and Neimark

[57] ABSTRACT

Disclosed are 2-amino-5-phenyl-1,3-benzodiazepines of the formula

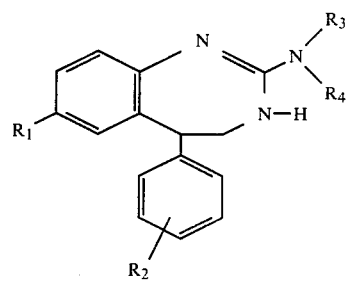

wherein $R_1$ and $R_2$ are hydrogen, halogen, alkyl, or alkoxy; $R_2$ being able to occupy any of the possible positions on the aromatic ring; $R_3$ is hydrogen or alkyl; and $R_4$ is hydrogen, alkyl, cycloalkyl, arylalkyl, heteroarylalkyl, dialkylaminoethyl, dialkylaminopropyl, (1-ethyl-2-pyrrolidino) methyl, dialkylamino, alkoxycarbonyl or cyano; or $R_3$ and $R_4$ form, with the adjacent nitrogen atom, a heterocycle having 5 to 7 side chains, optionally containing another heteroatom selected from oxygen, sulfur or nitrogen, this latter being able to be substituted by an alkyl group. The majority of the compounds are obtained by condensation of the corresponding 2-methylthio benzodiazepine hydroiodide with an appropriate amine. The compounds are useful as antidepressants.

12 Claims, No Drawings

2-AMINO-5-PHENYL-1,3-BENZODIAZEPINES

BACKGROUND OF THE INVENTION

This invention relates to substituted 2-amino-5-phenyl-4,5-3H-dihydro-1,3-benzodiazapines and a process for their preparation. The compounds have therapeutic use as antidepressants.

2-amino-7,8-dimethoxy-4,5-3H-dihydro-1,3-benzodiazepines have been described [Rodriquez, et al, *J. Org. Chem.* 33, 670 (1968)]. Other 2-amino-4,5-3H-dihydro-1,3-benzodiazepines unsubstituted in the 5 position have also been described in U.S. Pat. Nos. 3,780,203 and 3,780,024 as antihypertensive agents and depressants of the central nervous system. Further, 2-anilo-4,5-3H-dihydro-1,3-benzodiazepines have been suggested as diuretic agents in French Patent Application No. 82,13,605 filed by Bayssat, et al.

SUMMARY OF THE INVENTION

The compounds of the present invention are represented by the general formula I:

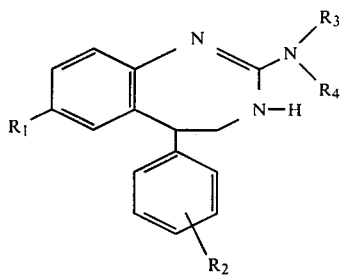

wherein $R_1$ and $R_2$ are hydrogen, a halogen, alkyl, or alkoxy, $R_2$ being able to occupy any of the possible positions on the aromatic ring; $R_3$ is hydrogen or alkyl; $R_4$ is hydrogen, alkyl, cycloalkyl, arylalkyl, heteroarylalkyl, dialkylaminoethyl, dialkylaminopropyl, (1-ethyl-2-pyrrolidino)methyl, dialkylamino, alkoxycarbonyl or cyano, with the proviso that when $R_4$ is cyano, $R_3$ is hydrogen; or else $R_3$ and $R_4$ form, with the adjacent nitrogen atom, a heterocycle having 5 to 7 side chains, optionally containing another heteroatom selected from oxygen, sulfur or nitrogen, which is unsubstituted or substituted with alkyl. The terms alkyl or alkoxy as used herein refer to straight or branched hydrocarbon radicals comprising from 1 to 4 carbon atoms. The term cycloalkyl as used herein refers to rings containing from 4 to 7 carbon atoms. By arylalkyl or heteroarylalkyl is meant the group of formula II Ar—alk—   II wherein Ar is a benzene ring, optionally mono- or polysubstituted by halogen, alkyl, alkoxy, nitro or amino. Ar can also be the 2-pyridyl, 3-pyridyl, 4-pyridyl or 2-furyl; alk- represents methylene, or an ethylene chain optionally substituted by a hydroxy group.

The compounds of formula I wherein $R_3$ is hydrogen and $R_4$ is hydrogen or alkoxycarbonyl constitute a particularly attractive class of compounds.

Pharmaceutically acceptable salts are of compounds of the formula I within the scope of the invention. These salts include salts prepared from compounds of the formula I with inorganic acids such as hydrochloric acid, hydrobromic acid, sulfuric acid, phosphoric acid, or from organic acids such as tartaric acid, citric acid, acetic acid, maleic acid, acid, oxalic acid, methanesulfonic acid, fumaric acid.

DETAILED DESCRIPTION OF THE INVENTION

The compounds of the invention, except those for which $R_4$ representa an alkoxycarbonyl cyano, are obtained by condensation of the derivatives of general formula III

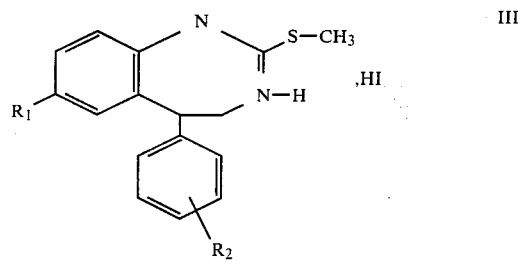

with an amine of general formula IV

In formula III and IV, $R_1$, $R_2$, $R_3$ and $R_4$ have the meanings given above.

The reaction is carried out in an inert organic solvent, at temperatures between ambient temperature and the boiling temperature of the solvent used, Solvents that have given the best results are alkanols and nitriles having a low molecular weight and N,N-dimethylformamide. Use of acetonitrile has been found to be particularly advantageous. The reaction time is a function of the temperature used and varies from 1 h to 60 h; preferably, temperatures close to the boiling point of the solvent are used where possible to minimize reation time.

Preparation of the compounds of formula III is described in French Patent Application 82.10,466[,published]

The compounds of the invention wherein $R_4$ is alkoxycarbonyl and, $R_1$, $R_2$, and $R_3$ have the meanings given above, are obtained by condensing a 2-amino-5-phenyl-1,3-benzodiazepine of general formula V

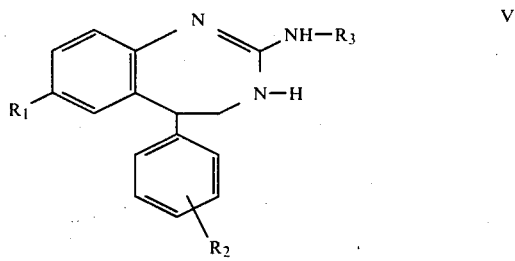

with an alkyl chloroformate of formula VI

wherein $R_5$ is alkyl. The reaction is performed in the presence of a base such as dilute soda, dilute potash or an alkaline carbonate.

The compounds of the invention wherein R₄ is cyano and R₃ is hydrogen (formula X) are obtained by the series of reactions below, wherein R₁ and R₂ have the meanings given above:

a diamine of formula VII whose preparation is described in French Patent Application 82.10,466 (supra):

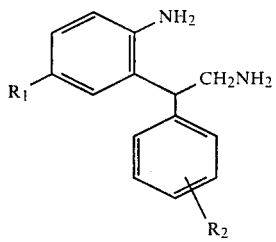

VII is condensed with a compound of formula VIII:

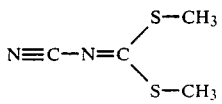

VIII to give the intermediate IX:

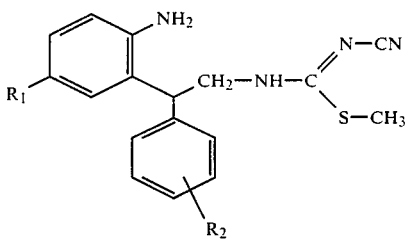

IX

IX is cyclized into X by heating in an organic solvent having a high boiling point, for example, from 90° C. to 110° C.:

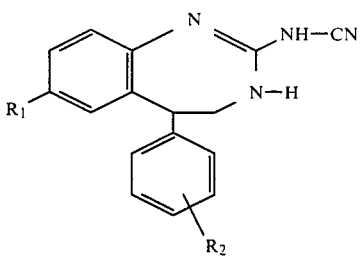

X

The compounds of invention represented by formula I affect the central nervous system and are clinically useful in the treatment of depressive states and psychic disturbances. The mood-modifying activity of the compounds is evaluated by standardized tests such as inhibition of known reserpine ptosis. Reserpine ptosis may be induced by methods such as those described in the literature. For example, Rubin, et al, [J. Pharmacol, Exp. Ther. 120: 125(1957)] induced ptosis in Swiss mice by intraperitoneal injection of 5 mg/kg of reserpine. This ptosis was marked 1 h 30 min later. Compounds to be tested for reserpine inhibition were administered orally at the same time as the reserpine was injected. The effective doses (ED$_{50}$) obtained for products of the invention and those obtained for the standard antidepressant amitriptyline [5-(3-dimethylaminopropylidene)dibenzo[a,d]-1,4-cycloheptadiene hydrochloride] are given in Table I:

TABLE I

| Products | Reserpine ptosis ED$_{50}$ (mg/kg/PO) |
|---|---|
| AMITRIPTYLINE | 10 |
| Example 1 | 18 |
| Example 3 | 10 |
| Example 4 | 11 |
| Example 8 | 3 |
| Example 48 | 13 |

Lethal doses (LD50) of these products as determined orally in Swiss mice are given in Table II:

TABLE II

| Products | LD$_{50}$ PO (mg/kg) |
|---|---|
| AMITRIPTYLINE | 150 |
| Example 1 | 600 |
| Example 3 | 330 |
| Example 4 | 1,200 |
| Example 8 | 2,400 |
| Example 48 | >3,200 |

Compounds of the formula I thus have clinical application as pharmaceuticals, particularly as antidepressants. These pharmaceuticals are conveniently administered orally in the form of plain or sugar-coated tablets or capsules, or rectally in the form of suppositories. The active ingredient is usually combined with various pharmaceutically compatible excipients. Daily dosages typically vary from 10 to 200 mg, depending on the seriousness of the condition being treated and patient idiosyncrasies.

Exemplary pharmaceutical formulations are given below:

A. Composition of a 100-mg tablet, optionally coated:

| active ingredient | 5 mg |
|---|---|
| lactose | 41 mg |
| wheat starch | 41 mg |
| gelatin | 2 mg |
| alginic acid | 5 mg |
| talc | 5 mg |
| magnesium stearate | 1 mg |

B. Composition of a capsule:

| active principle | 10 mg |
|---|---|
| lactose | 32 mg |
| wheat starch | 25 mg |
| talc | 2.5 mg |
| magnesium stearate | 0.5 mg |

The following examples are illustrative of the invention, without limitation:

EXAMPLE 1

2-Amino-5-phenyl-4,5-3H-dihydro-1,3-benzodiazepine hydrochloride

A mixture of 95.6 g (241.2 mmoles) of 2-methylthio-5-phenyl-4,5,3H-dihydro-1,3-benzodiazepine hydroiodide, 1250 cc of ethyl alcohol and 970 cc of 34% ammonia are refluxed together. About every 4 hours ammonia is bubbled until the reaction medium is saturated the reaction is continued until release of methanethiol stops (about 30 hours). After cooling, insoluble material is filtered and the filtrate is evaporated dry. The residue is dissolved with 500 cc of water then alkalized very strongly with potash pellets. The mixture is stirred for 1 hour with 200 cc of ether. The precipitate of 2-amino-5-phenyl-4,5-3H-dihydro-1,3-benzodiazepine is filtered, washed with water and dried. It is dissolved in ethyl alcohol and treated with 50 cc of 10N hydrochloric acid. The mixture is evaporated dry and the resulting 2-amino-5-phenyl-4,5-3H-dihydro-1,3-benzodiazepine hydrochloride is purified by recrystallization in an acetone-ethyl alcohol mixture. Yield: 42.3 g (64%); m.p.=215°-217° C.

IR (KBr): $\nu$ (C=N+): 1680 cm$^{-1}$.

NMR (DMSO d$_6$+D$_2$O) $\delta$=3.7-4.1 (complex mass, 2H); 4.4-4.7 (complex mass, 1H); 7.0-7.7 (multiplet, 9H).

Analysis by percent: $C_{15}H_{16}ClN_3$; M=273.76.

|  | C % | H % | Cl % | N % |
|---|---|---|---|---|
| Calculated | 65.80 | 5.89 | 12.95 | 15.35 |
| Found | 65.94 | 5.98 | 12.84 | 15.18 |

The products described in Examples 2 to 10 are obtained by operating under the conditions of example 1.

EXAMPLE 2

2-Amino-7-chloro-5-phenyl-4,5-3H-dihydro-1,3-benzodiazepine hydrochloride

Obtained from 7-chloro-2-methylthio-5-phenyl-4,5-3H-dihydro-1,3-benzodiazepine hydroiodide. m.p.=166°-168° C. (acetone-ethyl alcohol)

Analysis by percent: $C_{15}H_{15}Cl_2N_3$; M=308.20.

|  | C % | H % | Cl % | N % |
|---|---|---|---|---|
| Calculated | 58.45 | 4.91 | 23.01 | 13.63 |
| Found | 58.44 | 4.95 | 22.99 | 13.64 |

EXAMPLE 3

2-Amino-5-(4-methylphenyl)-4,5-3H-hydro-1,3-benzodiazepine hydrochloride

Obtained from 5-(4-methylphenyl)-2-methylthio-4,5-3H-dihydro-4,5-3H-benzodiazepine hydroiodide. m.p.=162°-163° C. (acetone-isopropyl alcohol)

Analysis by percent: $C_{16}H_{18}ClN_3$; M=287.78.

|  | C % | H % | Cl % | N % |
|---|---|---|---|---|
| Calculated | 66.77 | 6.30 | 12.32 | 14.60 |
| Found | 66.90 | 6.40 | 12.30 | 14.61 |

EXAMPLE 4

2-Amino-5-(4-chlorophenyl)-4,5-3H-dihydro-1,3-benzodiazepine hydrochloride

Obtained from 5-(4-chlorophenyl)2-methylthio-4,5-3H-dihydro-1,3-benzodiazepine hydroiodide. m.p.=163°-166° C. (acetone-ethyl alcohol)

Analysis by percent: $C_{15}H_{15}Cl_2N_3$; M=308.20.

|  | C % | H % | Cl % | N % |
|---|---|---|---|---|
| Calculated | 58.45 | 4.91 | 23.01 | 13.63 |
| Found | 58.60 | 4.93 | 22.90 | 13.61 |

EXAMPLE 5

2-Amino-5-(4-methoxyphenyl)-4,5-3H-dihydro-1,3-benzodiazepine hemioxalate

The base is prepared, according to Example 1, from 5-(4-methoxyphenyl)-2-methylthio-4,5-3H-dihydro-1,3-benzodiazepine hydroiodide. The hemioxalate is obtained by adding a solution of a demi-equivalent of oxalic acid in acetone to a solution of this base in acetone. m.p.=248°-249° C. (water-ethyl alcohol).

Analysis by percent: $C_{17}H_{18}N_3O_3$; M=312.33.

|  | C % | H % | N % |
|---|---|---|---|
| Calculated | 65.37 | 5.81 | 13.46 |
| Found | 65.06 | 6.03 | 13.29 |

EXAMPLE 6

2-Amino-7-methyl-5-phenyl-4,5-3H-dihydro-1,3-benzodiazepine hydrochloride

Obtained from 7-methyl-2-methylthio-5-phenyl-4,5-3H-dihydro-1,3-benzodiazepine hydroiodide. m.p.=159°-161° C. (isopropyl alcohol-diisopropyl ether).

Analysis by percent: $C_{16}H_{18}ClN_3$; M=287.78.

|  | C % | H % | Cl % | N % |
|---|---|---|---|---|
| Calculated | 66.77 | 6.30 | 12.32 | 14.60 |
| Found | 66.68 | 6.13 | 12.26 | 14.66 |

EXAMPLE 7

2-Amino-5-(3-methylphenyl)-4,5-3H-dihydro-1,3-benezodiazepine hydrochloride

Obtained from 5-(3-methylphenyl)-2-methylthio-4,5-3H-dihydro-1,3-benzodiazepine hydroiodide. m.p.=137°-139° C. (acetone-ethyl alcohol).

Analysis by percent: $C_{16}H_{18}ClN_3$; M=287.78.

|  | C % | H % | Cl % | N % |
|---|---|---|---|---|
| Calculated | 66.77 | 6.30 | 12.32 | 14.60 |
| Found | 66.66 | 6.57 | 12.36 | 14.46 |

EXAMPLE 8

2-Amino-7-methyl-5-(4-methylphenyl)-4,5-3H-dihydro-1,3-benzodiazepine hydrochloride Obtained from 7-methyl-5-(4-methylphenyl)-2-methylthio-4,5-3H-dihydro-1,3-benzodiazepine hydroiodide. m.p. 202°-203° C. (isopropyl alcohol-diisopropyl ether).

Analysis by percent: $C_{17}H_{20}ClN_3$; M=301.81.

|  | C % | H % | Cl % | N % |
|---|---|---|---|---|
| Calculated | 67.66 | 6.68 | 11.75 | 13.93 |
| Found | 67.65 | 6.55 | 11.74 | 13.99 |

EXAMPLE 9

2-Amino-7-chloro-5-(4-methylphenyl)-4.5-3H-dihydro-1,3-benzodiazepine hydrochloride Obtained from 7-chloro-5-(methylphenyl)-2-methylthio-4,5-3H-dihydro-1,3-benzodiazepine hydroiodide. m.p.=172°–174° C. (isopropyl alcohol-diisopropyl ether).

Analysis by percent: $C_{16}H_{17}Cl_2N_3$; M=322.23.

|  | C % | H % | Cl % | N % |
| --- | --- | --- | --- | --- |
| Calculated | 59.64 | 5.32 | 22.00 | 13.04 |
| Found | 59.96 | 5.10 | 21.97 | 13.09 |

EXAMPLE 10

2-Amino-5-(2-methylphenyl)-4,5-3H-dihydro-1,3-benzodiazepine hydrochloride

Obtained from 5-(2-methylphenyl)-2-methylthio-4,5-3H-dihydro-1,3-benzodiazepine hydroiodide. m.p.=243°–244° C. (isopropyl alcohol).

Analysis by percent: $C_{16}H_{18}ClN_3$; N=287.78.

|  | C % | H % | Cl % | N % |
| --- | --- | --- | --- | --- |
| Calculated | 66.77 | 6.30 | 12.32 | 14.60 |
| Found | 66.89 | 6.36 | 12.33 | 14.43 |

EXAMPLE 11

2-Dimethylamino-5-phenyl-4,5-3H-dihydro-1,3-benzodiazepine oxalate

2-Dimethylamino-5-phenyl-4,5-3H-dihydro-1,3-benzodiazepine is obtained from 2-methylthio-5-phenyl-4,5-3H-dihydro-1,3-benzodiazepine hydroiodide and dimethylamine by operating as in Example 1. The oxalate is obtained by addition of a solution of an equivalent of oxalic acid in acetone to a solution of the base in acetone. m.p.=196°–198° C. (acetone-methyl alcohol).

Anaysis by percent: $C_{19}H_{21}N_3O_4$; M=355.38.

|  | C % | H % | N % |
| --- | --- | --- | --- |
| Calculated | 64.21 | 5.93 | 11.82 |
| Found | 63.91 | 6.17 | 11.79 |

EXAMPLE 12

2-Methylamino-5-(4-methylphenyl)-4,5-3H-dihydro-1,3-benzodiazepine hydrochloride A mixture of 16.4 g of 5-(4-methylphenyl)-2-methylthio-4,5-3H-dihydro-1,3-benzodiazepine hydroiodide, 100 cc of ethyl alcohol and 20 cc of a 33% methylamine ethyl alcohol solution is refluxed. Every three hours 100 cc of the methylamine ethyl alcohol solution are added until release of methanethiol stops (about 12 hours). The reaction medium is then concentrated dry. The residue is dissolved with water and the mixture made strongly alkaline by addition of potash pellets and then extracted twice with methylene chloride. The collected organic phases are washed with water and dried on sodium sulfate. The methylene chloride is eliminated and 8 cc of 10N hydrochloric acid are added to the residue which is dissolved in ethyl alcohol. After evaporation to dryness, the 2-methylamino-5-(4-methylphenyl)-4,5-3H-dihydro-1,3-benzodiazepine hydrochloride is recrystallized in an isopropyl alcohol-diisopropylether mixture. m.p.=210°–211° C. Yield: 9.9 g (79%).

Analysis by percent: $C_{17}H_{20}ClN_3$; M=301.81.

|  | C % | H % | Cl % | N % |
| --- | --- | --- | --- | --- |
| Calculated | 67.66 | 6.68 | 11.75 | 13.93 |
| Found | 67.63 | 6.88 | 11.67 | 13.82 |

EXAMPLE 13

2-Methylamino-5-phenyl-4,5-3H-dihydro-1,3-benzodiazepine oxalate

2-Methylamino-5-phenyl-4,5-3H-dihydro-1,3-benzodiazepine is obtained, after treatment, from 2-methylthio-5-phenyl-4,5-3H-dihydro-1,3-benzodiazepine hydroiodide by operating as in example 12. After recrystallization in a hexane-ethyl acetate mixture melts at 142°–144° C.

An oxalic acid equivalent, dissolved in acetone, is added to this base, dissolved in acetone. The resulting oxalate is filtered and recrystallized in an acetone-ethyl alcohol mixture. m.p.=163°–165° C. Analysis by percent: $C_{18}H_{19}N_3O_4$; M=341.35.

|  | C % | H % | N % |
| --- | --- | --- | --- |
| Calculated | 63.33 | 5.61 | 12.31 |
| Found | 63.40 | 5.55 | 12.38 |

EXAMPLE 14

2-Benzylamino-5-phenyl-4,5-3H-dihdro-1,3-benzodiazepine hydrochloride

A mixture of 8 g (20 mmoles) of 2-methylthio-5-phenyl-4,5-3H dihydro-1,3-benzodiazepine hydroidide, 4.3 g (40 mmoles) of benzylamine and 50 cc of acetonitrile is refluxed under nitrogen, until release of methanethiol stops (about 7 hours). After cooling, the reaction mixture is diluted with ether. 2-Benzylamino-5-phenyl-4,5-3H-dihydro-1,3-benzodiazepine hydroiodide precipitates. It is filtered and put in suspension in water. The mixture is alkalinized with a soda solution and extracted with ether. The organic phase is washed with water and dried on sodium sulfate. The solvent is evaporated and the residue dissolved in ethyl alcohol. 5 cc of a 10N hydrochloric acid solution is added to this solution and concentrated under vacuum. 2-Benzylamino-5-phenyl-4,5-3H-dihydro-1,3-benzodiazepine hydrochloride is obtained which is purified by recrystallization in ethyl alcohol.

Yield: 4.9 g (67%), m.p.=206°–208° C.

Analysis by percent: $C_{22}H_{22}ClN_3$; M=363.88.

|  | C % | H % | Cl % | N % |
| --- | --- | --- | --- | --- |
| Calculated | 72.61 | 6.10 | 9.74 | 11.55 |
| Found | 72.39 | 6.17 | 9.80 | 11.60 |

The products described in examples 15 to 46 are prepared by operating under the conditions of example 14.

EXAMPLE 15

2-(4-Chlorobenzylamino)-5-phenyl-4,5-3H-dihydro-1,3-benzodiazepine hydrochloride Obtained by condensation of 4-chlorobenzylamine and 2-methylthio-5-phenyl-4,5-3H-dihydro-1,3-benzodiazepine hydroiodide. m.p.=181°–183° C. (acetone-ethyl alcohol).

Analysis by percent: $C_{22}H_{21}Cl_2N_3$; M=398.33.

|            | C %   | H %  | Cl %  | N %   |
|------------|-------|------|-------|-------|
| Calculated | 66.34 | 5.31 | 17.80 | 10.55 |
| Found      | 66.30 | 5.38 | 17.78 | 10.55 |

EXAMPLE 16

2-Benzylamino 7-chloro-5-phenyl-4,5-3H-dihydro-1,3-benzodiazepine hydrochloride

Obtained by condensation of benzylamine and 7-chloro-2-methylthio-5-phenyl-4,5-3H-dihydro-benzodiazepine hydroiodide. m.p. 169°–170° C. (acetone-ethyl alcohol).

Analysis by percent: $C_{22}H_{21}Cl_2N_3$; M=398.33.

|            | C %   | H %  | Cl %  | N %   |
|------------|-------|------|-------|-------|
| Calculated | 66.34 | 5.31 | 17.80 | 10.55 |
| Found      | 66.30 | 5.48 | 17.67 | 10.49 |

EXAMPLE 17

2-Benzylamino-5-(4-methylphenyl)4,5-3H-dihydro-1,3-benzodiazepine hydrochloride

Obtained by condensation of benzylamine and 5-(4-methylphenyl)-2-methylthio-4,5-3H-dihydro-1,3-benzodiazepine hydroiodide. m.p.=177°–178° C. (isopropyl alcohol).

Analysis by percent: $C_{23}H_{24}ClN_3$; M=377.90.

|            | C %   | H %  | Cl %  | N %   |
|------------|-------|------|-------|-------|
| Calculated | 73.10 | 6.40 | 9.38  | 11.12 |
| Found      | 72.94 | 6.49 | 9.46  | 11.06 |

EXAMPLE 18

2-Benzylamino-5-(4-methoxlphenyl)-4,5-3H-dihydro-1,3-benzodiazepine hydrochloride Obtained by condensation of benzylamine and 5-(4-methoxyphenyl)-2-methylthio-4,5-3H-dihydro-1,3-benzodiazepine hydroiodide. m.p.=120°–122° C. (acetone).

Analysis by percent: $C_{23}H_{24}ClN_3O$; M=393.90.

|            | C %   | H %  | Cl %  | N %   |
|------------|-------|------|-------|-------|
| Calculated | 70.13 | 6.14 | 9.00  | 10.67 |
| Found      | 70.16 | 6.06 | 9.05  | 10.66 |

EXAMPLE 19

2-Furfurylamino-5-phenyl-4,5-3H-dihydro-1,3-benzodiazepine hemioxalate

Obtained by condensation of furfurylamine and 2-methylthio-5-phenyl-4,5-3H-dihydro-1,3-benzodiazepine hydroiodide. m.p.=220°–222° C. (ethyl alcohol-dimethylformamide).

Analysis by percent: $C_{21}H_{20}N_3O_3$; M=362.39.

|            | C %   | H %  | N %   |
|------------|-------|------|-------|
| Calculated | 69.60 | 5.56 | 11.59 |
| Found      | 69.30 | 5.99 | 11.44 |

EXAMPLE 20

2-Benzylamino-5-(4-chlorophenyl)-4,5-3H-dihydro-1,3-benzodiazepine hydrochloride Obtained by condensation of benzylamine and 5-(4-chlorophenyl)-2-methylthio-4,5-3H-dihydro-1,3-benzodiazepine hydroiodide. m.p. 164°–166° C. (acetone-ethyl alcohol)

Analysis by percent: $C_{22}H_{21}Cl_2N_3$; M=398.33.

|            | C %   | H %  | Cl %  | N %   |
|------------|-------|------|-------|-------|
| Calculated | 66.34 | 5.31 | 17.80 | 10.55 |
| Found      | 66.22 | 5.53 | 17.66 | 10.49 |

EXAMPLE 21

2-(4-Chlorobenzylamino-5-(4-methylphenyl)-4,5-3H-dihydro-1,3-benzodiazepine hydrochloride Obtained by condensation of 4-chlorobenzylamine and 5-(4-methylphenyl)-2-methylthio-4,5-3H-dihyfro-1,3-benzodiazepine hydroiodide. m.p. 202°–203° C. (isopropyl alcohol-diisopropyl ether).

Analysis by percent: $C_{23}H_{23}Cl_2N_3$; M=412.34.

|            | C %   | H %  | Cl %  | N %   |
|------------|-------|------|-------|-------|
| Calculated | 67.00 | 5.62 | 17.20 | 10.19 |
| Found      | 66.96 | 5.96 | 17.26 | 10.19 |

EXAMPLE 22

2-(3-Methylbenzylamino)-5-phenyl-4,5-3H-dihydro-1,3-benzodiazepine hydrochloride Obtained by condensation of 3-methylbenzylamine and 2-methylthio-5-phenyl-4,5-3H-dihydro-1,3-benzodiazepine hydroiodide. m.p.=145°–146° C. (acetone-isopropyl alcohol).

Analysis by percent: $C_{23}H_{24}ClN_3$; M=377.90.

|            | C %   | H %  | Cl %  | N %   |
|------------|-------|------|-------|-------|
| Calculated | 73.10 | 6.40 | 9.38  | 11.12 |
| Found      | 72.99 | 6.45 | 9.48  | 11.06 |

EXAMPLE 23

2-Methoxybenzylamino)5-phenyl-4,5-3H-dihydro-1,3-benzodiazepine hydrochloride

Obtained by condensation of 4-methoxybenzylamine and 2-methylthio-5-phenyl-4,5-3H-dihydro-1,3-benzodiazepine hydroiodide. m.p.=202°–204° C. (acetone-ethyl alcohol).

Analysis by percent: $C_{23}H_{24}ClN_3O$; M=393.90.

| | C % | H % | Cl % | N % |
|---|---|---|---|---|
| Calculated | 70.13 | 6.14 | 9.00 | 10.67 |
| Found | 70.16 | 6.06 | 9.04 | 10.59 |

EXAMPLE 24

2-4-Methylbenzylamino)-5-phenyl-4,5-3H-dihydro-1,3-benzodiazepine hydrochloride

Obtained by condensation of 4-methylbenzylamine and 2-methylthio-5-phenyl-4,5-3H-dihydro-1,3-benzoiazepine hydroiodide. m.p. =176°–178° C. (acetone-ethyl alcohol).

Analysis by percent: $C_{23}H_{24}ClN_3$; M=377.90.

| | C % | H % | Cl % | N % |
|---|---|---|---|---|
| Calculated | 73.10 | 6.40 | 9.38 | 11.12 |
| Found | 73.16 | 6.10 | 9.50 | 11.30 |

EXAMPLE 25

2-Benzylamino-7-methyl-5-phenyl-4,5-3H-dihydro-1,3-benzodiazepine hydrochloride

Obtained by condensation of benzylamine and 7-methyl-2-methylthio-5-phenyl-4,5-3H-dihydro-1,3-benzodiazepine hydroiodide. m.p. =153°–155° C. (acetone-isopropyl alcohol).

Analysis by percent: $C_{23}H_{24}ClN_3$; M=377.90.

| | C % | H % | Cl % | N % |
|---|---|---|---|---|
| Calculated | 73.10 | 6.40 | 9.38 | 11.12 |
| Found | 73.10 | 6.20 | 9.41 | 11.22 |

EXAMPLE 26

2-(2-Methylbenzylamino)-5-phenyl-4,5-3H-dihydro-1,3-benzodiazepine hydrochloride Obtained by condensation of 2-methylbenzylamine and 2-methylthio-5-phenyl-4,5-3H-dihydro-1,3-benzodiazepine hydroiodide. m.p. 131°–133° C. (acetone-diisopropyl ether).

Analysis by percent: $C_{23}H_{24}Cln_3$; M=377.90.

| | C % | H % | Cl % | N % |
|---|---|---|---|---|
| Calculated | 73.10 | 6.40 | 9.38 | 11.12 |
| Found | 73.10 | 6.16 | 9.39 | 11.26 |

EXAMPLE 27

2-Benzylamino-5-(3-methylphenyl)-4,5-3H-dihydro-1,3-benzodiazepine hydrochloride Obtained by condensation of benzylamine and 5-(3-methylphenyl)-2-methylthio-4,5-3H-dihydro-1,3-benzodiazepine hydroiodide. m.p=159°–161° C. (acetone-ethyl alcohol).

Analysis by percent: $C_{23}H_{24}ClN_3$; M=377.90.

| | C % | H % | Cl % | N % |
|---|---|---|---|---|
| Calculated | 73.10 | 6.40 | 9.98 | 11.12 |
| Found | 73.05 | 6.45 | 9.40 | 11.06 |

EXAMPLE 28

2-Benzylamino-5-(2-methylphenyl)4,5-3H-dihydro-1,3-benzo diazepine hydrochloride Obtained by condensation of benzylamine and 5-(2-methylphenyl-2-methylthio-4,5-3H-dihydro-1,3-benzodiazepine hydroiodide. m.p.=163°–164° C. (isopropyl alcohol-diisopropyl ether)

Analysis by percent: $C_{23}H_{24}ClN_3$; M=377.90.

| | C % | H % | Cl % | N % |
|---|---|---|---|---|
| Calculated | 73.10 | 6.40 | 9.38 | 11.12 |
| Found | 72.90 | 6.60 | 9.40 | 11.08 |

EXAMPLE 29

2-(2,3-Dimethylbenzylamino)-5-phenyl-4,5-3H-dihydro-1,3-benzodiazepine hydrochloride Obtained by condensation of 2,3-dimethylbenzylamine and 2-methylthio-5-phenyl-4,5-3H-dihydro-1,3-benzodiazepine hydroiodide. m.p. 207°–209° C. (ethyl alcohol).

Analysis by percent: $C_{24}H_{26}ClN_3$; M=391.92.

| | C % | H % | Cl % | N % |
|---|---|---|---|---|
| Calculated | 73.55 | 6.69 | 9.05 | 10.72 |
| Found | 73.60 | 6.69 | 9.06 | 10.69 |

EXAMPLE 30

2-(2,6-Dimethylbenzylamino)-5-phenyl-4,5-3H-dihydro-1,3-benzodiazepine hydrochloride Obtained by condensation of 2,6-dimethylbenzylamine and 2-methylthio-5-phenyl-4,5-3H-dihydro-1,3-benzodiazepine hydroiodide. m.p. 165°–169° C. (ethyl alcohol).

Analysis by percent: $C_{24}H_{26}ClN_3$; M=391.92.

| | C % | H % | Cl % | N % |
|---|---|---|---|---|
| Calculated | 73.55 | 6.69 | 9.05 | 10.72 |
| Found | 73.44 | 6.88 | 9.04 | 10.69 |

EXAMPLE 31

2-Benzylamino-7-chloro-5-(4-methylphenyl)-4,5-3H-dihyro-1,3-benzodiazepine hydrochloride Obtained by condensation of benzylamine and 7-chloro-5-(4-methylphenyl)-2-methylthio-4,5-3H-dihydro-1,3-benzodiazepine hydroiodide. m.p.=184°–186° C. (ethyl alcohol).

Analysis by percent: $C_{23}H_{23}Cl_2N_3$; M=412.35.

| | C % | H % | Cl % | N % |
|---|---|---|---|---|
| Calculated | 67.00 | 5.62 | 17.20 | 10.19 |
| Found | 67.06 | 5.88 | 16.89 | 10.23 |

EXAMPLE 32

2-Benzylamino-7-methyl-5-(4-methylphenyl)-4,5-3H-dihydro-1,3-benzodiazepine hydrochloride Obtained by condensation of benzylamine and 7-methyl-5-(4-methylphenyl)-2-methylthio-4,5-3H-dihydro-1,3-benzodiazepine hydroiodide. m.p. 204°-205° C. (isopropyl alcohol-diisopropyl ether).

Analysis by percent: $C_{24}H_{26}ClN_3$; M=391.92.

|  | C % | H % | Cl % | N % |
|---|---|---|---|---|
| Calculated | 73.55 | 6.69 | 9.05 | 10.72 |
| Found | 73.77 | 6.70 | 8.98 | 10.63 |

EXAMPLE 33

5-Phenyl-2-(2-pyridylmethylamino)-4,5-3H-dihydro-1,3-benzodiazepine dihydrochloride Obtained by condensation of 2-aminomethyopyridine and 2-methylthio-5-Phenyl-4,5-3H-dihydro-1,3-benzodiazapine hydroiodide. m.p.=253°-255° C. (ethyl alcohol-dimethylformamide).

Analysis by percent: $C_{21}H_{22}Cl_2N_4$; M=401.33.

|  | C % | H % | Cl % | N % |
|---|---|---|---|---|
| Calculated | 62.85 | 5.53 | 17.67 | 13.96 |
| Found | 62.86 | 5.66 | 17.56 | 13.96 |

EXAMPLE 34

5-Phenyl-2-(3-pyridylmethylamino)-4,5-3H-dihydro-1,3-benzodiazepine dihydrochloride Obtained by condensation of 3-aminomethylpyridine and 2-methylthio-5-phenyl-4,5-3H-dihydro-1,3-benzodiazepine hydroiodide, m.p. 210°-212° C. (acetone-ethyl alcohol).

Analysis by percent: $C_{21}H_{22}Cl_2N_4$; M=401.33.

|  | C % | H % | Cl % | N % |
|---|---|---|---|---|
| Calculated | 62.85 | 5.53 | 17.67 | 13.96 |
| Found | 62.90 | 5.55 | 17.62 | 14.03 |

EXAMPLE 35

5-Phenyl-2-(4-pyridylmethylamino)-4,5-3H-dihydro-1,3-benzodiazepine dihydrochloride Obtained by condensation of 4-aminomethylpyridine and 2-methylthio-5-phenyl-4,5-3H-dihydro-1,3-benzodiazepine hydroiodide. m.p.=251°-253° C. (ethyl alcohol).

Analysis by percent: $C_{21}H_{22}Cl_2N_4$; M=401.33.

|  | H % | Cl % | N % |
|---|---|---|---|
| Calculated | 62.85 | 5.53 | 17.67 | 13.96 |
| Found | 62.89 | 5.60 | 17.63 | 13.98 |

EXAMPLE 36

2-(4-Nitrobenzylamino)-5-phenyl-4,5-3H-dihydro-1,3-benzodiazepine oxalate

Obtained by condensation of 4-nitrobenzylamine and 2-methylthio-5-phenyl-4,5-3H-dihydro-1,3-benzodiazepine hydroiodide. m.p.=160°-162° C. (acetone-ethyl alcohol).

Analysis by percent: $C_{26}H_{22}N_4O_6$; M=462.45.

|  | C % | H % | N % |
|---|---|---|---|
| Calculated | 62.33 | 4.80 | 12.09 |
| Found | 62.38 | 4.86 | 12.13 |

EXAMPLE 37

2-(3-Amino-4-chlorobenzylamino)-5-phenyl-4,5-3H-dihydro-1,3-benzodiazepine maleate Obtained by condensation of 3-amino-4-chlorobenzylamine and 2-methylthio-5-phenyl-4,5-3H-dihydro-1,3-benzodiazepine hydroiodide. m.p.=166°-168° C. (acetone-ethyl alcohol).

Analysis percent: $C_{26}H_{25}ClN_4O_4$; M=492.95.

|  | C % | H % | Cl % | N % |
|---|---|---|---|---|
| Calculated | 63.35 | 5.11 | 7.19 | 11.37 |
| Found | 63.21 | 5.15 | 7.22 | 11.23 |

EXAMPLE 38

2-(4-Aminobenzylamino)-5-phenyl-4,5-3H-dihydro-1,3-benzodiazepine dihydrochloride Obtained by condensation of 4-aminobenzylamine and 2-methylthio-5-phenyl-4,5-3H-dihydro-1,3-benzodiazepine hydroiodide. m.p.=188°-190° C. (ethyl alcohol-ether).

EXAMPLE 39

2-Cyclopentylamino-5-phenyl-4,5-dihydro-1,3-benzodiazepine hydrochloride

Obtained by condensation of cyclopentylamine and 2-methylthio-5-phenyl-4,5-dihydro-1,3-benzodiazepine hydroiodide. m.p.=181°-183° C. (acetone alcohol).

Analysis by percent: $C_{20}H_{24}ClN_3$; M=341.87.

|  | C % | H % | Cl % | N % |
|---|---|---|---|---|
| Calculated | 70.26 | 7.07 | 10.37 | 12.29 |
| Found | 70.08 | 7.08 | 10.46 | 12.36 |

EXAMPLE 40

2-[Amino(3-dimethylaminopropyl)]-5-phenyl-4,5-3H-dihydro-1,3-benzodiazepine dihydrochloride Obtained by condensation of 3-dimethylaminopropylamine and 2-methylthio-5-phenyl-4,5-3H-dihydro-1,3-benzodiazepine hydroiodide. m.p.=185°-187° C. (acetone-ethyl alcohol).

Analysis by percent: $C_{20}H_{28}Cl_2N_4$; M=395.36.

|  | C % | H % | Cl % | N % |
|---|---|---|---|---|
| Calculated | 60.74 | 7.14 | 17.93 | 14.17 |
| Found | 60.48 | 7.47 | 17.86 | 14.15 |

EXAMPLE 41 CL

7-Chloro-2-[amino(3-dimethylaminopropyl)[-5-phenyl-4,5-3H-dihydro-1,3-benzodiazepine dioxalate Obtained by condensation of 3-dimethylaminopropylamine and 7-chloro-2-methylthio-5-phenyl-4,5-3H-dihydro-1,3-benzodiazepine hydroiodide. m.p. 186°-188° C. (ethyl alcohol).

Analysis by percent: $C_{24}H_{29}ClN_4O_8$; M=536.96.

|  | C % | H % | Cl % | N % |
|---|---|---|---|---|
| Calculated | 53.68 | 5.44 | 6.60 | 10.43 |
| Found | 53.26 | 5.66 | 6.61 | 10.37 |

EXAMPLE 42

2-[Amino(2-dimethylaminoethyl)-5-phenyl-4,5-3H-dihydro-1,3-benzodiazepine dihydrochloride Obtained by condensation of 2-dimethylaminoethylamine and 2-methylthio-5-phenyl-4,5-3H-dihydro-1,3-benzodiazepine hydroiodide. m.p.=223°-225° C. (acetone-ethyl alcohol).

Analysis by percent: $C_{19}H_{26}Cl_2N_4$; M=381.34.

|  | C % | H % | Cl % | N % |
|---|---|---|---|---|
| Calculated | 59.84 | 6.87 | 18.60 | 14.70 |
| Found | 59.50 | 7.35 | 18.48 | 14.70 |

EXAMPLE 43

2-Phenethylamino-5-phenyl-4,5-3H-dihydro-1,3-benzodiazepine hydrochloride

Obtained by condensation of 2-phenylethylamine and 2-methylthio-5-phenyl-4,5-3H-dihydro-1,3-benzodiazepine hydroiodide. m.p. 164°-166° C. (acetone-ethyl alcohol).

Analysis by percent: $C_{23}H_{24}ClN_3$; M=377.90.

|  | C % | H % | Cl % | N % |
|---|---|---|---|---|
| Calculated | 73.10 | 6.40 | 9.38 | 11.12 |
| Found | 73.06 | 6.44 | 9.40 | 11.06 |

EXAMPLE 44

2-(4-Methyl-1-piperazinyl)-5-phenyl-4,5-3H-dihydro-1,3-benzodiazepine dihydrochloride, hydrate Obtained by condensation of N-methylpiperazine and 2-methylthio-5-phenyl-4,5-3H-dihydro-1,3-benzodiazepine dydroiodide. m.p.=193°-194° C. (ethyl alcohol-diisopropyl ether).

Analysis by percent: $C_{20}H_{27}Cl_2N_4O$; M=410.36.

|  | C % | H % | Cl % | N % | O % |
|---|---|---|---|---|---|
| Calculated | 58.53 | 6.63 | 17.28 | 13.65 | 3.90 |
| Found | 58.23 | 6.84 | 17.23 | 13.52 | 4.04 |

EXAMPLE 45

2-[Methylamino(1-ethyl-2-pyrrolidinyl)]-5-phenyl-4,5-3H-dihydro-1,3-benzodiazepine dihydrochloride Obtained by condensation of 2-aminomethyl-1-ethyl-pyrrolidine and 2-methylthio-5-phenyl-4,5-3H-dihydro-1,3-benzodiazepine hydroiodide. m.p.=242°-245° C. (ethyl alcohol).

Analysis by percent: $C_{22}H_{30}Cl_2N_4$; M=421.40.

|  | C % | H % | Cl % | N % |
|---|---|---|---|---|
| Calculated | 62.70 | 7.18 | 16.83 | 13.30 |
| Found | 62.85 | 7.13 | 16.83 | 13.26 |

EXAMPLE 46

2-[Amino(2-hydroxy-2-phenylethyl)]-5-phenyl-4,5-3H-dihydro-1,3,benezodiazepine

Obtained by condensation of 2-amino-1-phenylethyl alcohol and 2-methylthio-5-phenyl-4,5-3H-dihydro-1,3-benzodiazepine hydroiodide. m.p.=174°-176° (ethyl alcohol).

Analysis by percent: $C_{23}H_{23}N_3O$; M=357.43.

|  | C % | H % | N % |
|---|---|---|---|
| Calculated | 77.28 | 6.48 | 11.76 |
| Found | 77.36 | 6.43 | 11.86 |

EXAMPLE 47

2-(2,2-Dimethylhydrazino)-5-phenyl-4,5-3H-dihydro-1,3-benzodiazepine hydrochloride A mixture of 25 g (63 mmoles) of 2-methylthio-5-phenyl-4,5-3H-dihydro-1,3-benzodiazepine hydroiodide, 56.8 g (950 mmoles) of 1,1-dimethylhydrazine and 300 cc of N,N-dimethylformamide is brought to 60° C. for 40 hours. The reaction mixture is concentrated under low pressure. The residue is dissolved in water, strongly alkalized by potash pellets and extracted with methylene chloride. The organic phase is washed with a water and dried on sodium sulfate. After elimination of the solvent, 2-(2,2-dimethylhydrazino)-5-phenyl-4,5-3H-dihydro-1,3-benzodiazepine is collected and converted to its hydrochloride by the usual method. m.p.=160°-162° C. (ethyl alcohol-ethyl acetate).

Analysis by percent: $C_{17}H_{21}ClN_4$; M=316.83.

|  | C % | H % | Cl % | N % |
|---|---|---|---|---|
| Calculated | 64.45 | 6.68 | 11.19 | 17.69 |
| Found | 64.55 | 6.60 | 11.19 | 17.60 |

EXAMPLE 48

2-amino-(5-Phenyl-4,5-3H-dihydro-1,3-benzodiazepin)yl ethyl carbamate 1.95 g (18 mmoles) of ethyl chloroformate are added drop by drop, then a mixture of 50 cc of water and 50 g of crushed ice is added to a suspension of 8.3 g (35 mmoles) of 2-amino-5-phenyl-4,5-3H-dihydro-1,3-benzodiazepine in a mixture of 50 cc of water and 50 g of crush ice. 1.95 g (18 mmoles) of ethyl chloroformate and a solution of 1.5 g (37.5 mmoles) of soda in 10 cc of water are then added simultaneously. it is allowed to return to an ambient temperature and stirred for another hours. The precipitate is filtered, washed with water and dried. It is purified by recrystallization in ethyl alcohol. m.p.=209°-211° C.

Yield: 4.9 g (39%). IR: $\nu(C=O)=1680$ cm$^{-1}$.

Analysis by percent: $C_{18}H_{19}N_3O_2$; M=309.35.

|  | C % | H % | N % |
|---|---|---|---|
| Calculated | 69.88 | 6.19 | 13.58 |

| | C % | H % | N % |
|---|---|---|---|
| Found | 69.98 | 5.96 | 13.54 |

EXAMPLE 49

[2-(5-Phenyl-4,5-3H-dihydro-1,3-benzodiazepin)yl]-cyanamide

A solution of 25.4 g (120 mmoles of 2-(2-aminophenyl)-2-phenylethylamine in 120 cc of ethyl alcohol is added drop by drop to a solution of 17.5 g (120 mmoles) of dimethyl cyanodithioimidocarbonate in 100 cc of ethyl alcohol. Stirring is continued for 1 hour at ambient temperature and the mixture is left standing overnight. The precipitate is filtered, washed with a little ethyl alcohol and dried. It is put into solution in 200 cc of N,N-dimethylformamide. The solution is refluxed for 30 hours and then evaporated dry under low pressure. The residue is purified by recrystallization in a methyl alcohol-N,N-dimethylformamide mixture. The [2-(5-phenyl-4,5-3H-dihydro-1,3-benzodiazepine)yl]cyanamide melts at 261°–263° C.

Yield: 14.8 g (47%). IR: $\nu$ (C≡N)=2160 cm$^{-1}$.
Analysis by percent: $C_{16}H_{14}N_4$; M=262.30.

| | C % | H % | N % |
|---|---|---|---|
| Calculated | 73.26 | 5.38 | |
| Found | 73.32 | 5.25 | 21.44 |

It is to be understood that the present invention is not limited to the embodiments disclosed which are illustratively offered and that modifications may be made without departing from the invention.

What is claimed is:

1. A 2-amino-5-phenyl-1,3-benzodiazepine, of the formula I

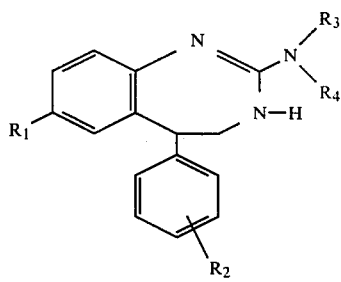

wherein $R_1$ and $R_2$ are hydrogen, halogen, $C_1$–$C_4$ alkyl, $C_1$–$C_4$ alkoxy, with $R_2$ capable of occupying any vacant position on the aromatic ring; $R_3$ is hydrogen or $C_1$–$C_4$ alkyl; $R_4$ is hydrogen; $C_1$–$C_4$-alkyl; $C_4$–$C_7$ cycloalkyl; arylalkyl or heteroarylalkyl of the formula Ar-Alk wherein Ar is pyridyl, 2-furyl, unsubstituted phenyl or phenyl mono- or poly-substituted with halogen, $C_1$–$C_4$-alkyl, $C_1$–$C_4$ alkoxy, nitro, or amino, and Alk is methylene or ethylene substituted or unsubstituted with hydroxy; di($c_1$–$C_4$-alkyl)aminoethyl; di($C_1$–$C_4$-alkyl)amino; $C_1$–$C_4$-alkoxycarbonyl; or cyano with the proviso that when $R_4$ is cyano, $R_3$ is hydrogen; or $R_3$ and $R_4$ form, with the adjacent nitrogen atom, methyl piperazinyl;

or a pharmaceutically acceptable salt thereof.

2. A 2-amino-5-phenyl-1,3-benzodiazepine, of the formula I

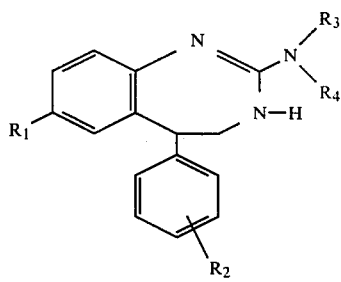

wherein $R_1$ and $R_2$ are hydrogen, halogen, $C_1$–$C_4$ alkyl, $C_1$–$C_4$ alkoxy, with $R_2$ capable of occupying any vacant position on the aromatic ring; $R_3$ is hydrogen or $C_1$–$C_4$ alkyl; $R_4$ is hydrogen; $C_1$–$C_4$-alkyl; $C_4$–$C_7$ cycloalkyl; arylalkyl or heteroarylalkyl of the formula Ar-Alk wherein Ar is pyridyl, 2-furyl, unsubstituted phenyl or phenyl mono- or poly-substituted with halogen, $C_1$–$C_4$-alkyl, $C_1$–$C_4$ alkoxy, nitro, or amino, and Alk is methylene or ethylene substituted or unsubstituted with hydroxy; di($C_1$–$C_4$-alkyl)aminoethyl; di($C_1$–$C_4$)-alkylaminopropyl; (1-ethyl-2-pyrrolidino)methyl; di($C_1$–$C_4$-alkyl)amino; $C_1$–$C_4$-alkoxycarbonyl; or cyano with the proviso that when $R_4$ is cyano, $R_3$ is hydrogen; or $R_3$ and $R_4$ form, with the adjacent nitrogen atom, pyridyl or piperazinyl unsubstituted or substituted with $C_1$–$C_4$-alkyl;

or a pharmaceutically acceptable salt thereof.

3. The benzodiazepine of claim 1, wherein $R_4$ is alkoxycarbonyl.

4. The benzodiazepine of claim 1, wherein $R_3$ and $R_4$ are hydrogen.

5. A process for preparing the compound of claim 1, wherein $R_4$ is other than $C_1$–$C_4$-alkoxycarbonyl or cyano, comprising condensing a benzodiazepine of the formula

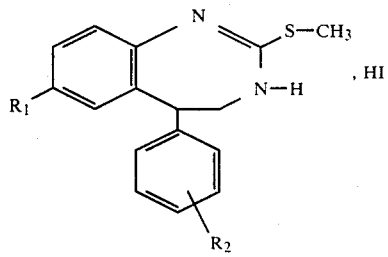

with an amine of the formula $R_3$—NH—$R_4$.

6. A process for preparing the compound of claim 1, wherein $R_4$ is $C_1$–$C_4$ alkoxycarbonyl, comprising treating a 2-amino=1,3-benzodiazepine of the formula

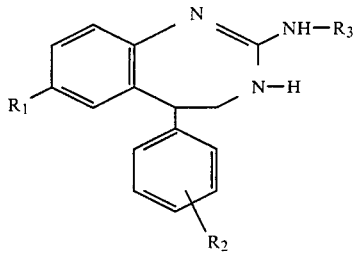

with an alkyl chloroformate of the formula Cl—COOR$_5$, wherein R$_5$ is C$_1$-C$_4$-alkyl.

7. A process for preparing the compound of claim 1 wherein R$_4$ is cyano and R$_3$ is hydrogen, comprising condensing a diamine of the formula

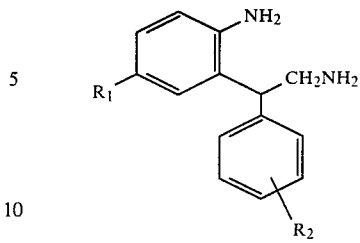

with a compound of the formula

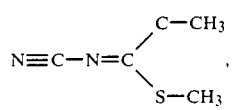

followed by cyclization of the condensation product by heating in an organic solvent having a high boiling point.

8. An antidepressant composition comprising an antidepressant amount of a compound of claim 1 and a pharmaceutically acceptable excipient.

9. The pharmaceutical composition of claim 8, wherein R$_3$ is hydrogen and R$_4$ is hydrogen or C$_1$-C$_4$-alkoxycarbonyl.

10. A method for treating depression in mammals comprising administering a compound of claim 1 to said mammal in an amount sufficient to alleviate depression.

11. The method of claim 10, wherein in the compound of claim 1, R$_3$ is hydrogen and R$_4$ is hydrogen or C$_1$-C$_4$-alkoxycarbonyl.

12. A method according to claim 10 wherein said amount administered is 10–200 mg per day.

* * * * *